US011123122B2

(12) United States Patent
Rezach et al.

(10) Patent No.: US 11,123,122 B2
(45) Date of Patent: Sep. 21, 2021

(54) ANATOMY BUTTRESSING ADAPTOR

(71) Applicant: Warsaw Orthopedic, Inc., Warsaw, IN (US)

(72) Inventors: William Alan Rezach, Covington, TN (US); David H. Browning, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 16/287,700

(22) Filed: Feb. 27, 2019

(65) Prior Publication Data
US 2020/0268423 A1    Aug. 27, 2020

(51) Int. Cl.
| | | |
|---|---|---|
| *A61B 17/86* | (2006.01) | |
| *A61F 2/44* | (2006.01) | |
| *A61B 17/80* | (2006.01) | |

(52) U.S. Cl.
CPC .......... *A61B 17/86* (2013.01); *A61F 2/4405* (2013.01); *A61B 17/809* (2013.01); *A61B 2017/8655* (2013.01)

(58) Field of Classification Search
CPC . A61B 17/861; A61B 17/863; A61B 17/8695; A61B 2017/8655; A61B 17/7032; A61B 17/7037; A61B 17/86
See application file for complete search history.

(56) References Cited

U.S. PATENT DOCUMENTS

| | | | | |
|---|---|---|---|---|
| 6,248,108 B1* | 6/2001 | Tormala | ............. | A61B 17/8625 411/533 |
| 7,909,826 B2* | 3/2011 | Serhan | ............... | A61B 17/1671 606/75 |
| 8,491,641 B2 | 7/2013 | Nihalani | | |
| 8,808,339 B2* | 8/2014 | Varela | ................ | A61B 17/8872 606/319 |
| 8,998,966 B2* | 4/2015 | Yap | .................... | A61B 17/8625 606/305 |
| 8,998,968 B1* | 4/2015 | Brow | ................. | A61B 17/8605 606/319 |
| 9,078,707 B2* | 7/2015 | Helgerson | .......... | A61B 17/3421 |
| 9,119,678 B2* | 9/2015 | Duggal | ............. | A61B 17/8695 |
| 9,414,865 B2* | 8/2016 | Duggal | ................ | A61B 17/808 |

(Continued)

FOREIGN PATENT DOCUMENTS

| | | |
|---|---|---|
| JP | 2004-512899 | 4/2004 |
| KR | 20150097279 | 8/2015 |

(Continued)

OTHER PUBLICATIONS

U.S. Appl. No. 15/843,938, filed Dec. 15, 2017 in the name of May et al.

(Continued)

*Primary Examiner* — Anu Ramana

(57) ABSTRACT

A screw and an anatomy buttressing adaptor are provided. The screw includes a head portion, a shaft portion, and a central axis. The anatomy buttressing adaptor includes a body portion including a first end, an opposite second end, a lower surface, and an internal cavity extending through the body portion. The lower surface of the body portion being formed at least adjacent the second end thereof, and including spikes formed thereon and spaced therearound.

14 Claims, 17 Drawing Sheets

(56) References Cited

U.S. PATENT DOCUMENTS

| | | | |
|---|---|---|---|
| 9,421,054 B2* | 8/2016 | Varela | A61B 17/8891 |
| 9,707,013 B2 | 7/2017 | Rezach et al. | |
| 9,770,277 B2* | 9/2017 | Biedermann | A61B 17/8685 |
| 9,872,711 B2 | 1/2018 | Hynes et al. | |
| 9,883,948 B2 | 2/2018 | Chavarria et al. | |
| 9,949,776 B2 | 4/2018 | Mobasser et al. | |
| 9,962,171 B2 | 5/2018 | Rezach et al. | |
| 9,974,569 B2 | 5/2018 | Lehmann, Jr. et al. | |
| 9,993,270 B2 | 6/2018 | Butler | |
| 10,028,770 B2 | 7/2018 | Rezach et al. | |
| 10,172,650 B2 | 1/2019 | Hynes et al. | |
| 2006/0217713 A1* | 9/2006 | Serhan | A61B 17/704 606/263 |
| 2006/0235393 A1 | 10/2006 | Bono et al. | |
| 2006/0241596 A1 | 10/2006 | Rezach | |
| 2007/0233138 A1 | 10/2007 | Figueroa et al. | |
| 2008/0255622 A1* | 10/2008 | Mickiewicz | A61B 17/7064 606/319 |
| 2009/0192551 A1* | 7/2009 | Cianfrani | A61B 17/685 606/301 |
| 2010/0094356 A1* | 4/2010 | Varela | A61B 17/862 606/304 |
| 2011/0313466 A1 | 12/2011 | Butler et al. | |
| 2011/0313472 A1* | 12/2011 | Yap | A61B 17/7064 606/305 |
| 2011/0319925 A1* | 12/2011 | Helgerson | A61B 17/3421 606/198 |
| 2012/0065691 A1 | 3/2012 | Simonson | |
| 2017/0245898 A1 | 8/2017 | May et al. | |

FOREIGN PATENT DOCUMENTS

| | | |
|---|---|---|
| KR | 101671434 | 11/2016 |
| WO | WO2006102110 | 9/2006 |
| WO | WO2010104496 | 9/2010 |

OTHER PUBLICATIONS

U.S. Appl. No. 16/380,739, filed Apr. 10, 2019 in the name of Rezach et al.

U.S. Appl. No. 16/386,328, filed Apr. 17, 2019 in the name of Rezach et al.

U.S. Appl. No. 16/395,319, filed Apr. 26, 2019 in the name of Wickham et al.

U.S. Appl. No. 16/395,409, filed Apr. 26, 2019 in the name of Wickham et al.

International Search Report and Written Opinion dated Feb. 11, 2020 from corresponding International Application No. PCT/US2019/057576.

International Search Report and Written Opinion dated Feb. 6, 2020 from corresponding International Application No. PCT/US2019/056643.

* cited by examiner

ANATOMY BUTTRESSING ADAPTOR

FIELD

The present technology is generally related to an anatomy buttressing adaptor.

BACKGROUND

Facet joints are formed between articular processes of adjacent vertebrae. Facet joints serve in guiding and limiting movement between the adjacent vertebrae. However, facet joints can degenerate due to, for example, disease, dislocation, fracture, trauma, etc., and such degeneration can cause pain. To aid elimination of the pain caused by such degeneration, facet screws have been used in fixing the articular processes relative to one another and such fixation can serve in limiting pain caused by such movement. Buttressing adaptors have been used to increase the connection force afforded by the facet screws. The buttressing adaptors are used to provide a platform with which forces afforded by the interaction of the threads and the bone can be applied by the screw heads through the buttressing adaptors to the bone. Therefore, there is a need for improved buttressing adaptors and/or adaptors that can be used with modular bone screws to facilitate application of such forces.

SUMMARY

The techniques of this disclosure generally relate to one or more adaptors usable with facet screws or other types of anatomy buttressing.

In one aspect, the present disclosure provides a system including a screw having a head portion, a shaft portion, and a central axis; and the anatomy buttressing adaptor including a body portion having a first end, an opposite second end, an internal cavity extending through the body portion, a first opening into the internal cavity at the first end of the body portion, and a second opening into the internal cavity at the second end of the body portion, the internal cavity having a central axis extending through the first end and the second end of the body portion, the body portion including a lower surface adjacent the second opening, spikes formed on and spaced around the lower surface of the body portion, and a flange formed on the body portion and extending into the internal cavity, and the flange being positioned at least adjacent the second end of the body portion, where at least a portion of the screw is insertable through the first opening, the internal cavity, and the second opening, at least a portion of the head portion is confinable within the internal cavity, and the screw, during confinement of the at least a portion of the head portion within the internal cavity, is rotatable about the central axis thereof and is pivotal relative to the central axis of the body portion.

In another aspect, the disclosure provides a system including a screw having a head portion, a shaft portion, and a central axis; a hub including a body portion having a first end, an opposite second end, an internal cavity extending through the body portion, a first opening into the internal cavity at the first end of the body portion, a second opening into the internal cavity at the second end of the body portion, the internal cavity having a central axis extending through the first end and the second end of the body portion, the hub including at least two protrusions formed on the body portion and extending into the internal cavity, an interior flange formed on the body portion and extending into the internal cavity, and an exterior flange formed on the body portion and extending outwardly therefrom, the at least two protrusions being positioned intermediate the first end and the second end of the body portion, the interior flange being positioned at least adjacent the second end of the body portion, and the exterior flange being positioned intermediate the first end and the second end of the body portion; and an anatomy buttressing adaptor including an upper surface, an opposite lower surface, an internal cavity extending between the upper surface and the lower surface, and a channel positioned between the upper surface and the lower surface, the lower surface including spikes formed thereon and spaced therearound, and the channel communicating with the internal cavity, and the internal cavity including a central axis; where at least a portion of the screw is insertable through the first opening, the internal cavity, and the second opening, at least a portion of the head portion is confinable within the internal cavity between the at least two protrusions and the flange, and the screw, during confinement of the at least a portion of the head portion within the internal cavity, is rotatable about the central axis thereof and is pivotal relative to the central axis of the body portion; and where at least portions of the screw and the hub are insertable through the internal cavity of the anatomy buttressing adaptor, at least a portion of the body portion is confinable within the internal cavity of the anatomy buttressing adaptor, at least a portion of the exterior flange of the hub is receivable within the channel, and the hub, during confinement of the at least a portion of the body portion within the internal cavity of the anatomy buttressing adaptor and receipt of the at least a portion of the exterior flange in the channel, is rotatable about the central axis of the internal cavity thereof.

In yet another aspect, the disclosure provides a system including a screw having a head portion, a shaft portion, and a central axis; a hub including a body portion having a first end, an opposite second end, an internal cavity extending through the body portion, a first opening into the internal cavity at the first end of the body portion, a second opening into the internal cavity at the second end of the body portion, the internal cavity having a central axis extending through the first end and the second end of the body portion, the hub including at least two protrusions formed on the body portion and extending into the internal cavity, an interior flange formed on the body portion and extending into the internal cavity, and an exterior flange formed on the body portion and extending outwardly therefrom, the at least two protrusions being positioned intermediate the first end and the second end of the body portion, the interior flange being positioned at least adjacent the second end of the body portion, and the exterior flange being positioned intermediate the first end and the second end of the body portion; and an anatomy buttressing adaptor including an upper surface, an opposite lower surface, and an aperture extending between the upper surface and the lower surface, the upper surface including a plurality of posts formed thereon and spaced therearound, the lower surface including spikes formed thereon and spaced therearound, the posts extending upwardly from the upper surface; where at least a portion of the screw is insertable through the first opening, the internal cavity, and the second opening, at least a portion of the head portion is confinable within the internal cavity between the at least two protrusions and the flange, and the screw, during confinement of the at least a portion of the head portion within the internal cavity, is rotatable about the central axis thereof and is pivotal relative to the central axis of the body portion; and where at least portions of the screw and the hub are insertable through the aperture of the anatomy buttressing adaptor, at least a portion of the body portion is confinable with the aperture of the anatomy buttressing adaptor, at least a portion of the exterior flange is engageable to the upper surface and the posts of the anatomy buttressing adaptor, at least a portion of the exterior flange of the hub is receivable within the channel, and the hub, during confinement of the at least a portion of the body portion with the aperture of the anatomy buttressing adaptor and engagement of the at least the exterior flange to the portions of the upper surface and the posts, is rotatable about the central axis of the aperture therethrough.

The details of one or more aspects of the disclosure as set forth in the accompanying drawings and the description below. Other features, objects, and advantages of the techniques described in this disclosure will be apparent from the description and drawings, and from the claims.

DETAILED DESCRIPTION

Figure 1:
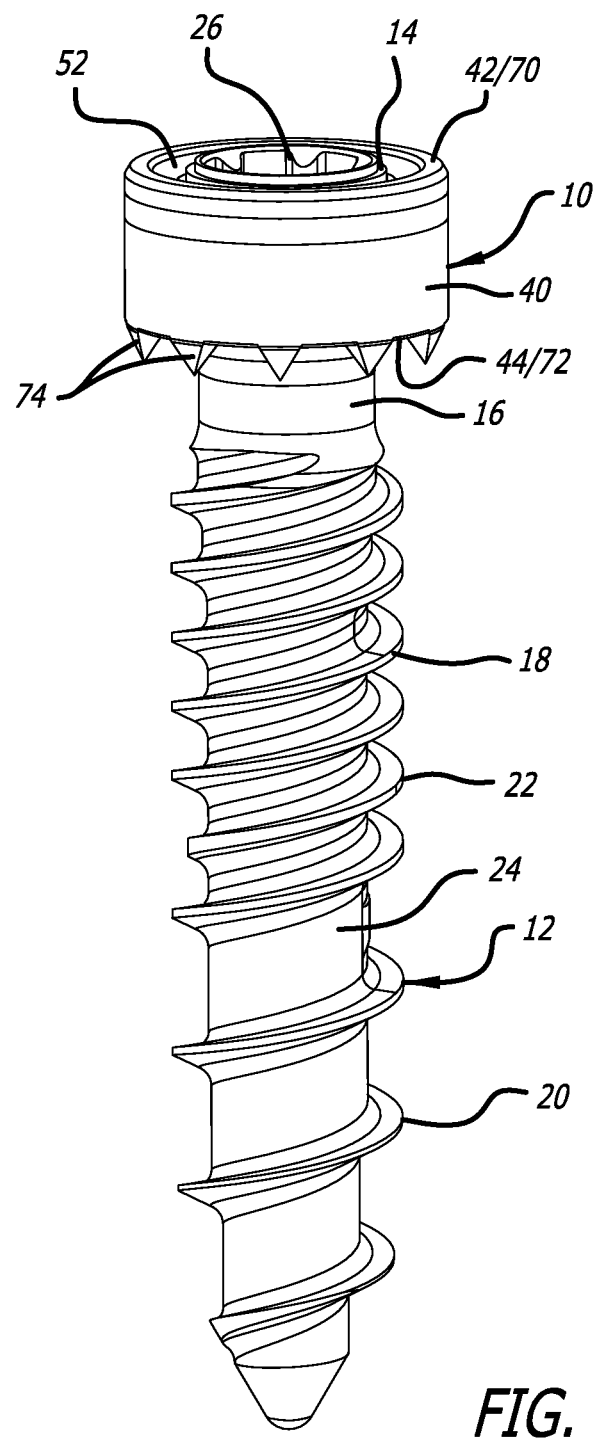
FIG. 1 is a top, front perspective view that illustrates a first embodiment of an anatomy buttressing adaptor assembled with a screw.
Figure 2:
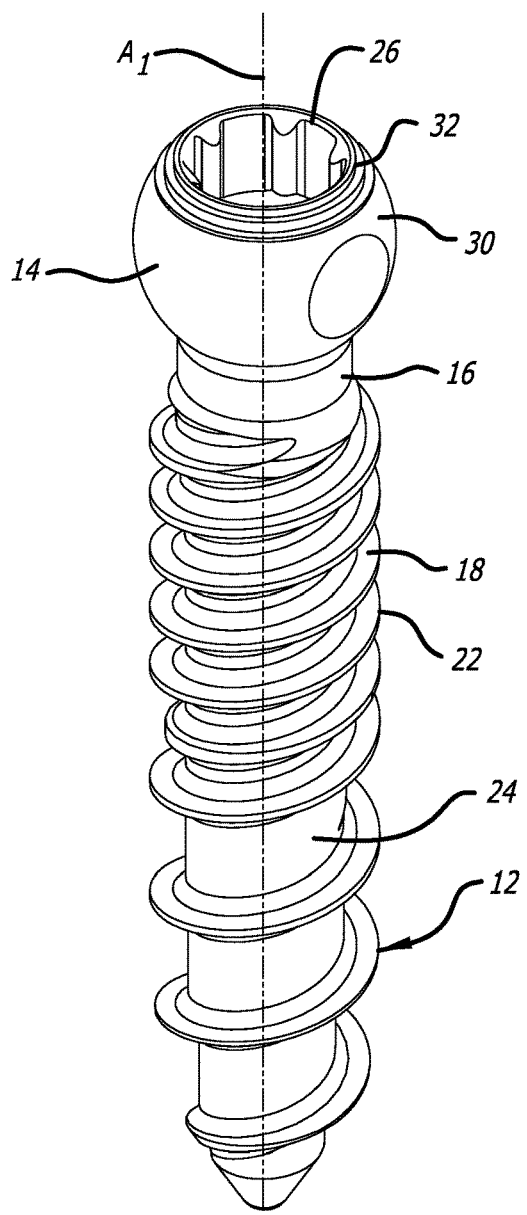
FIG. 2 is an exploded, top, front perspective view that illustrates the adaptor and the screw of FIG. 1.
Figure 2:
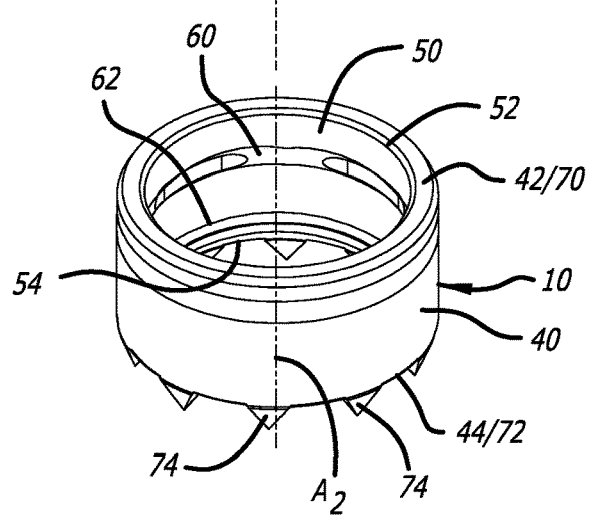
Figure 3:
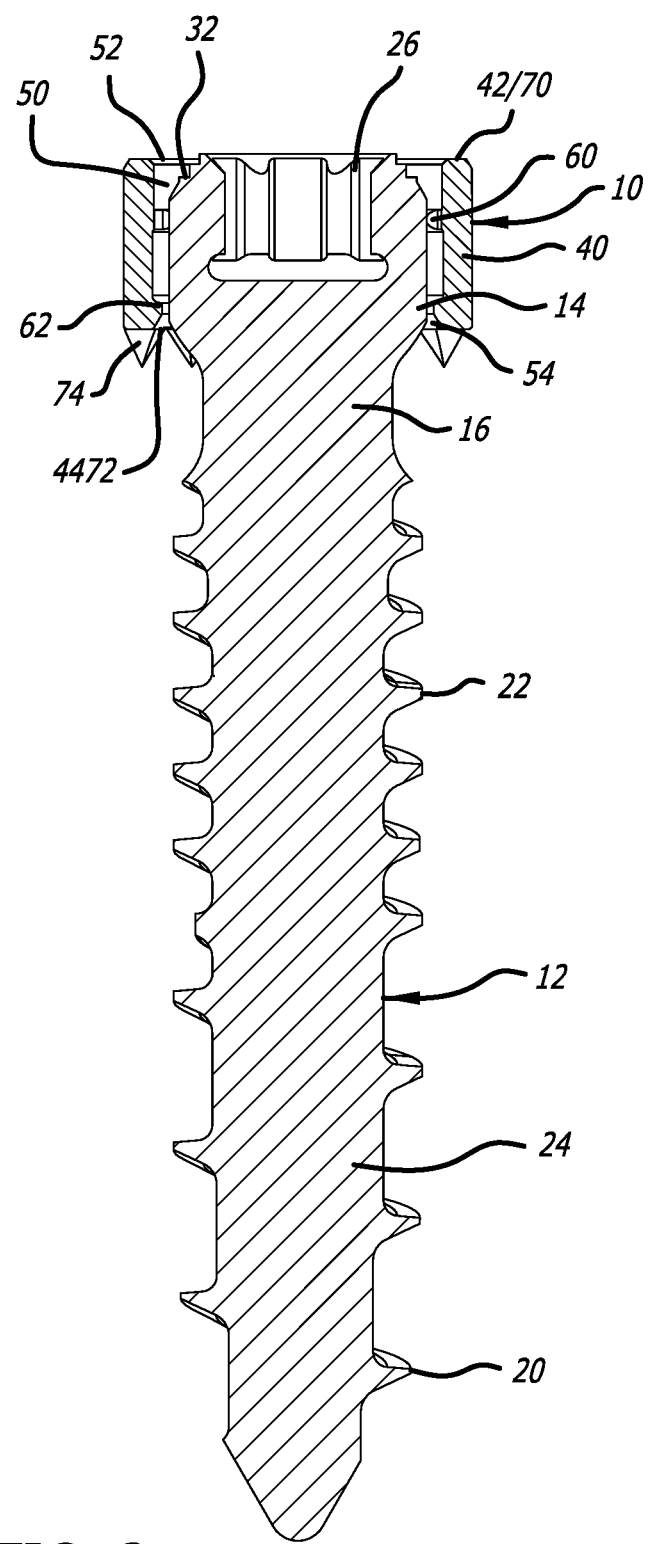
FIG. 3 is an elevational, side, cross-sectional view that illustrates the assembled adaptor and the screw of FIG. 1.

An anatomy buttressing adaptor according to an embodiment of the present disclosure is generally indicated by the numeral 10 in FIGS. 1-3. As depicted in FIGS. 1-3, the adaptor 10 can be used with a fastener such as a screw 12. As discussed below, the screw 12 can be used to fixedly attach the adaptor 10 and the screw 12 to tissue such as, for example, bone. The screw 12 can be substantially identical to screws disclosed in U.S. Ser. No. 15/054,384 (U.S. Patent Publication 2017/0245898), which is herein incorporated by reference in its entirety. The screws disclosed in U.S. Ser. No. 15/054,384 have previously been used as pedicle screws.

The screw 12 includes a head portion 14, a neck portion 16, a shaft portion 18, and a central axis $A_1$. As depicted in FIGS. 1-3, the head portion 14 is generally spherical, the neck portion 16 joins the shaft portion 18 to the head portion 14, and the shaft portion 18 is configured to penetrate tissue such as, for example, bone. The shaft portion 18 can include one or more thread forms having a continuous turn or discrete turns and/or different pitches to facilitate such bone penetration. As depicted in FIGS. 1-3, the shaft portion 18 includes a first thread form 20 and a second thread form 22 having a continuous turn and different pitches around a shank 24. Besides facilitating bone penetration, the first thread form 20 and the second thread form 22 are used in securing the screw 12 and the adaptor 10 to the bone. Furthermore, the shank 24 can have a smaller or a larger diameter than the neck portion 16, and can include portion(s) having tapered and/or cylindrical configurations.

The head portion 14 includes a tool-engaging portion 26 configured to engage a surgical tool or instrument for rotating the screw 12. As depicted in FIGS. 1-3, the tool-engaging portion 26 includes six (6) lobes arranged in a generally hexagonal cross-sectional configuration. In some embodiments, the tool-engaging portion 26 can have, for example, alternative cross-sectional configurations such as being generally polygonal (including generally triangular, rectangular, hexagonal, etc. configurations), oval, or irregular.

The head portion 14 includes an exterior surface 30, and, as depicted in FIG. 2, the exterior surface 30 is generally spherical. The exterior surface 30 includes a plurality of ridges 32 provided adjacent the tool-engaging portion 26. The ridges 32 can be used to improve purchase of the head portion 14 with other surgical instrumentation, such as that disclosed in U.S. Ser. No. 15/054,384.

As depicted in FIGS. 1-3, the adaptor 10 includes a generally cylindrical body portion 40, a first end 42, and a second end 44. The adaptor 10 includes an internal cavity 50 extending through the body portion 40, a first opening 52 into the internal cavity 50 at the first end 42, a second opening 54 into the internal cavity 50 at the second end 44, and a central axis $A_2$ extending through the internal cavity 50, the first opening 52, and the second opening 54. To facilitate attachment of the adaptor 10 to the screw 12, the first opening 52 is sized to receive the head portion 14 therethrough, and the internal cavity 50 is also sized to receive at least a portion of the head portion 14 therein. The head portion 14 is retained in the internal cavity 50 via various protrusions (or nubs) 60 and a flange 62. The protrusions 60 are formed on the body portion 40 and extend into the internal cavity 50, and the flange 62 is also formed on the body portion 40 and extends into the internal cavity 50 and defines the second opening 54. There can be at least two and preferably three or fourth protrusions 60 provided on the body portion 40. When inserted into the internal cavity 50, the head portion 14 can be pushed past the protrusions 60, snap-fit into position between the protrusions 60 and the flange 62, and seated against the flange 62. The flange 62 prevents at least a portion of the head portion 14 from exiting the internal cavity 50 via the second opening 54, and at least a portion of the head portion 14 is confined in the internal cavity 50 between the protrusions 60 and the flange 62.

When a portion of the head portion 14 of the screw 12 is confined in the internal cavity 50, the screw 12 is capable of rotation about its central axis $A_1$ relative to the adaptor 10, and also capable of pivotal rotation relative to the adaptor 10. Rotation of the screw 12 about its central axis $A_1$ relative to the adaptor 10 allows the screw 12 to be driven by a surgical tool or instrument, and pivotal rotation of the screw 12 relative to the adaptor 10 allows the angle of the central axis $A_1$ to be angularly adjusted relative to the angle of the axis $A_2$ of the internal cavity 50.

As such, the internal cavity 50 is configured to retain a portion of the head portion 14 thereon, while simultaneously allowing the head portion 14 to rotate therein. Thus, as discussed below, a surgical tool or instrument engaged to the tool-engaging portion 26 can used rotate the screw 12 relative to the adaptor 10.

As depicted in FIGS. 1-3, the adaptor 10 includes an upper surface 70 at the first end 42 of the body portion 40, and a lower surface 72 at the second end 44 of the body portion 40. The upper surface 70 and the lower surface 72 can be annular, and the lower surface 72 can include various protrusions 74 for engaging bone spaced therearound. As depicted in FIGS. 1-3, the protrusions 74 are spikes formed on (e.g., unitarily formed on) the lower surface 72 and configured to engage bone. As depicted in FIG. 1, for example, the spikes 74 can be formed as pyramids.

During use of the adaptor 10 and the screw 12, a portion of the head portion 14 of the screw 12 can initially be inserted through the second opening 54 into the internal cavity 50 of the adaptor 10 to facilitate attachment therebetween. Next, a surgical tool or instrument can be engaged to the tool-engaging portion 26. The screw 12 can then be driven into bone via rotation thereof using the surgical tool or instrument. Due to friction between the adaptor 10 and the head portion 14 of the screw 12, the adaptor 10 rotates with the screw 12 until the spikes 74 of the adaptor 10 ultimately contact and catch on the bone. When contacted and caught on the bone, the spikes 74 hold the adaptor 10 in position relative to the bone and prevent further rotation thereof. Given that the screw 12 can rotate relative to the adaptor 10, the screw 12 can continue to be driven into the bone until the adaptor 10 and the screw 12 are seated against the bone.

Alternatively, rather than being initially attached to the head portion 14 of the screw 12, the adaptor 10 can be attached to head portion 14 after the screw 12 is at least partially driven into bone. Thereafter, the screw 12 can be further driven into the bone until the adaptor 10 and the screw 12 are seated against the bone.

Figure 5:
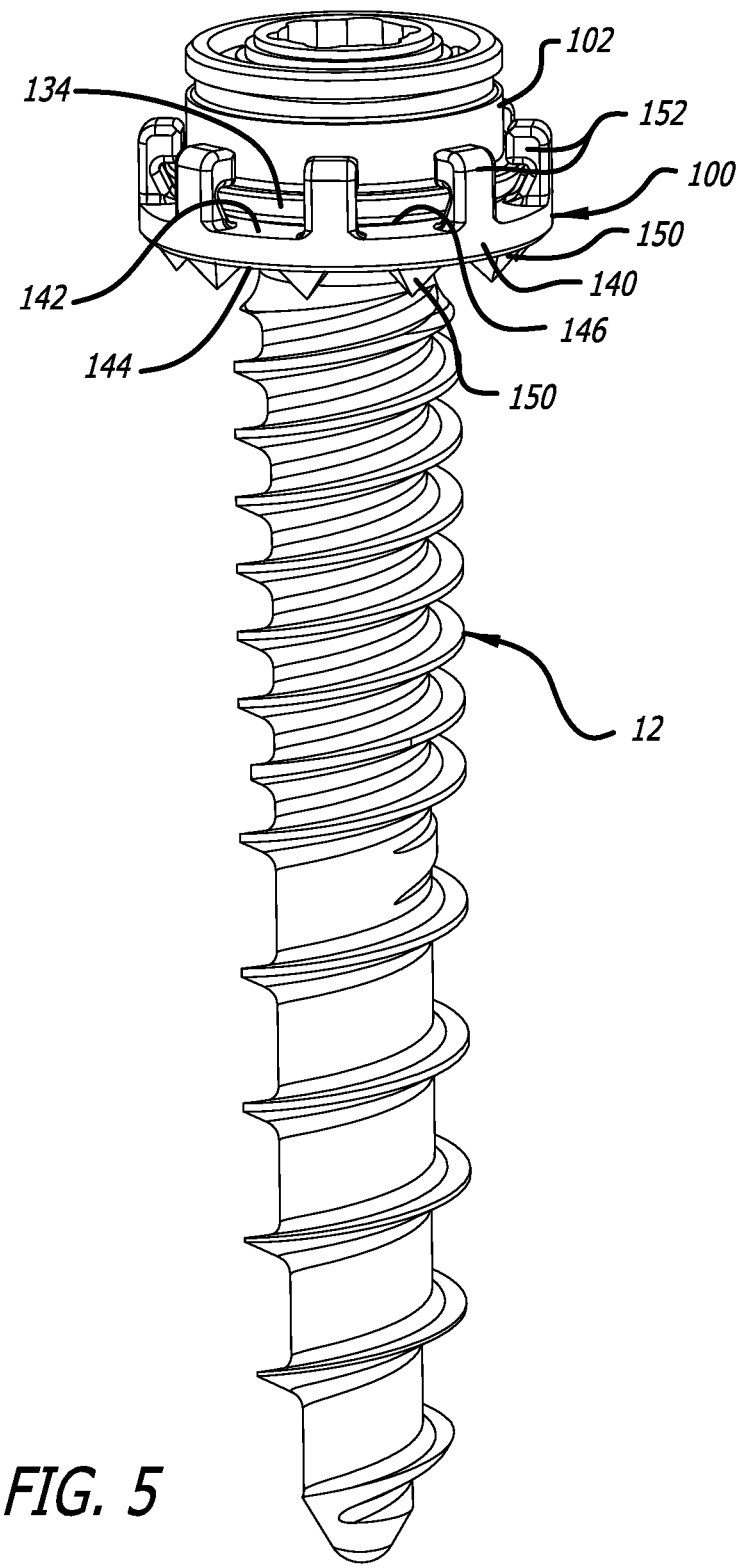
FIG. 5 is a top, front perspective view that illustrates a second embodiment of an anatomy buttressing adaptor assembled with the hub of FIG. 4 and a screw.
Figure 6:
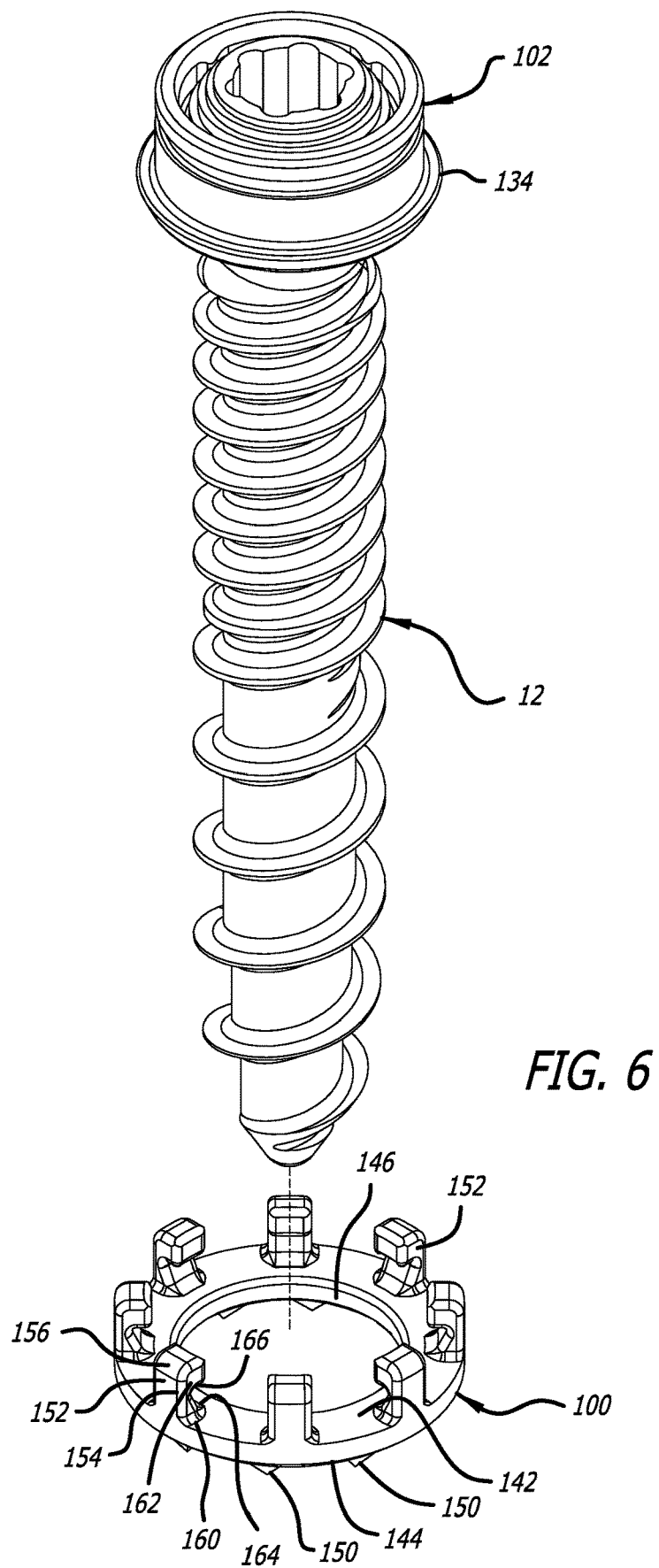
FIG. 6 is a partially exploded, top, front perspective view that illustrates the adaptor, the hub, and the screw of FIG. 5.
Figure 7:
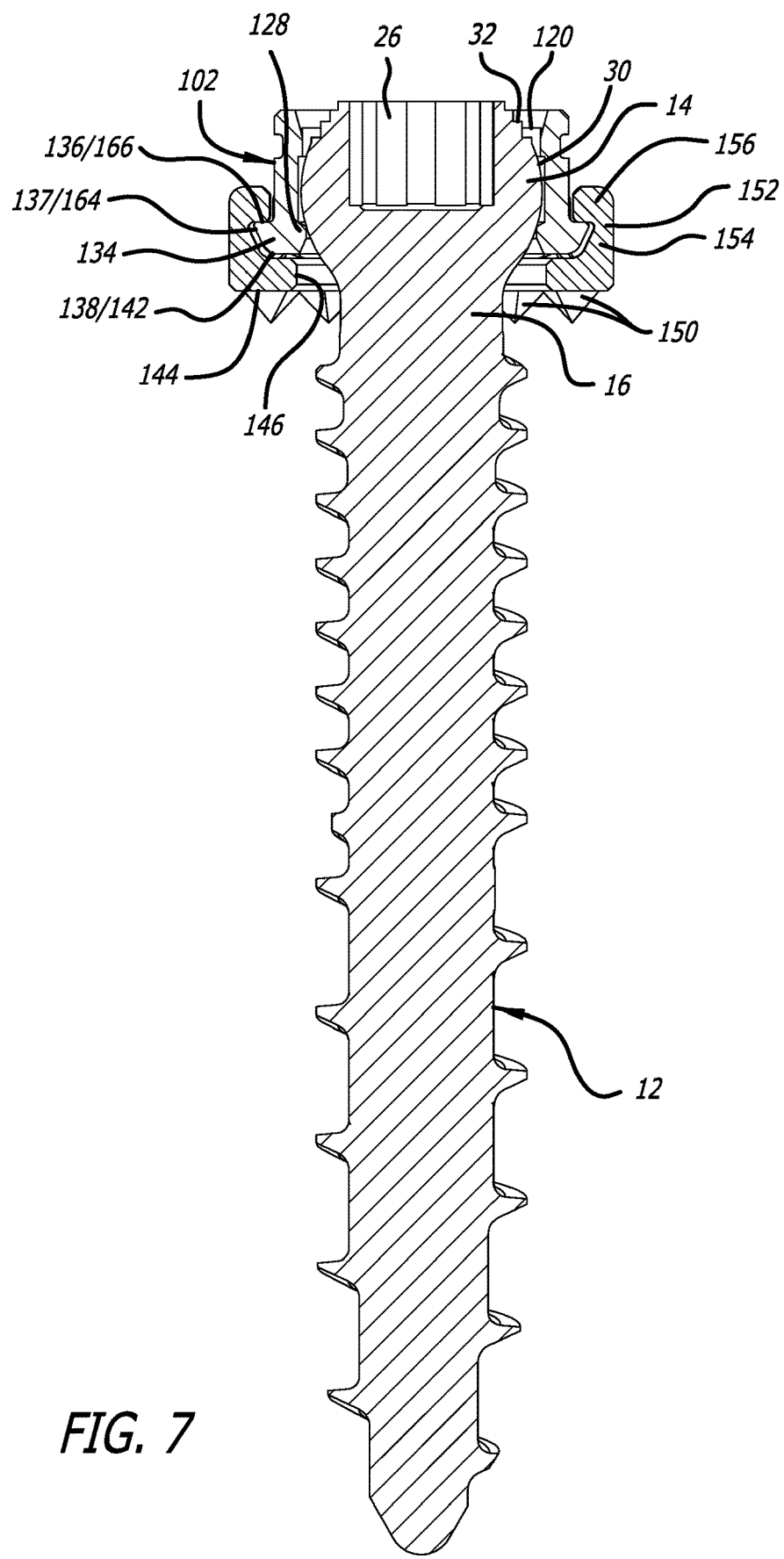
FIG. 7 is an elevational, side, cross-sectional view that illustrates the assembled adaptor, the hub, and the screw of FIG. 5.

An anatomy buttressing adaptor according to another embodiment of the present disclosure is generally indicated by the numeral 100 in FIGS. 5-7. The adaptor 100 can be used with a hub (or base) 102 and a fastener such as the screw 12. The adaptor 100 is attached to the hub 102, and the hub 102 and the screw 12 are attached to one another. The screw 12 then can be used to fixedly attach at least the adaptor 100, the hub 102, and the screw 12 to tissue such as, for example, bone.

Figure 4:
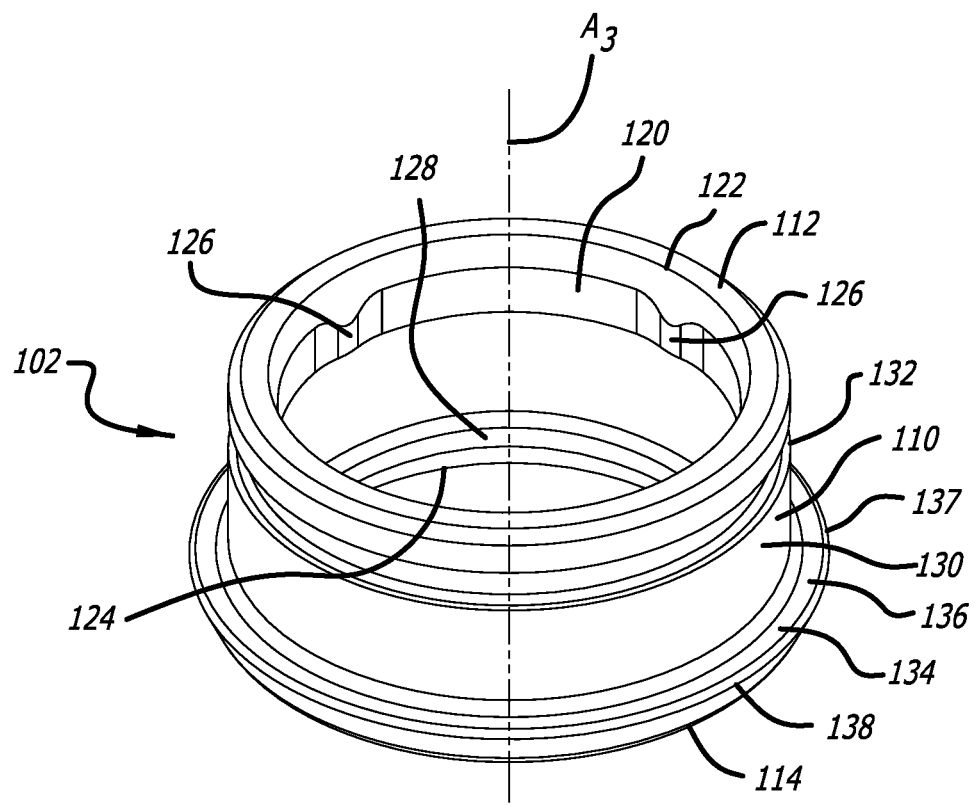
FIG. 4 is a top, front perspective view that illustrates a hub for use with additional embodiments of anatomy buttressing adaptors.

As depicted in FIG. 4, the hub 102 includes a generally cylindrical body portion 110, a first end 112, and a second end 114. The hub 102 includes an internal cavity 120 extending through the body portion 110, a first opening 122 into the internal cavity 120 at the first end 112, a second opening 124 into the internal cavity 120 at the second end 114, a central axis $A_3$ extending through the internal cavity 120, the first opening 122, and the second opening 124. To facilitate attachment of the hub 102 and the screw 12 to one another, the first opening 122 is sized to receive the head portion 14 therethrough, and the internal cavity 120 is also sized to receive at least a portion of the head portion 14 therein. The head portion 14 is retained in the internal cavity 110 via various protrusions (or nubs) 126 and a flange 128. The protrusions 126 are formed on the body portion 110 and extend into the internal cavity 120, and the flange 128 is also formed on the body portion 110 and extends into the internal cavity 120 and defines the second opening 124. The can be at least two and preferably three or four protrusions 126 provided on the body portion 110. When inserted into the internal cavity 120, the head portion 14 can be pushed past the protrusions 126, snap-fit into position between the protrusions 126 and the flange 128, and seated against the flange 128. The flange 128 prevents at least a portion of the head portion 14 from exiting the internal cavity 120 via the second opening 124, and at least a portion of the head portion 14 is confined in the internal cavity 120 between the protrusions 126 and the flange 128.

When a portion of the head portion 14 of the screw 12 is confined in the internal cavity 50, the screw 12 is capable of rotation about its central axis $A_1$ relative to the hub 102, and also capable of pivotal rotation relative to the hub 102. Rotation of the screw 12 about its central axis $A_1$ relative to the hub 102 allows the screw 12 to be driven by a surgical tool or instrument, and pivotal rotation of the screw 12 relative to the hub 102 allows the angle of the central axis $A_1$ to be angularly adjusted relative to the angle of the axis $A_3$ of the internal cavity 120.

Additionally, the body portion 110 includes an exterior surface 130, a groove 132, and a flange 134. As depicted in FIGS. 5-7, the groove 132 and the flange 134 are annular and extend around the exterior surface 130. The groove 132 and the flange 134 can be identical to similar structures disclosed in U.S. Ser. No. 15/054,384. As depicted in FIGS. 5-7, the flange 134 facilitates attachment of the adaptor 100 to the hub 102, and includes an upper surface 136, an intermediate surface 137, and lower surface 138.

As depicted in FIGS. 5-7, the adaptor 100 includes a base portion 140 that can be formed as an annular structure having an upper surface 142, a lower surface 144, and an aperture 146 extending between the upper surface 142 and the lower surface 144. The upper surface 142 and the lower surface 144 can be annular, the lower surface 144 can include various protrusions 150 for engaging bone spaced therearound, and the upper surface 142 can include various posts 152 spaced therearound. As depicted in FIGS. 5-7, the protrusions 150 are spikes formed on (e.g., unitarily formed on) the lower surface 144 and configured to engage bone, and the posts 152 are catches formed on (e.g., unitarily formed on) the upper surface 142 and configured to engage portions of the flange 134. As depicted in FIG. 5, for example, the spikes 150 can be formed as pyramids, and, as discussed below, the flange 134 of the hub 102 is ultimately clamped between the upper surface 142 and the catches 152.

As depicted in FIGS. 5-7, each of the catches 152 are deflectable and generally "L" shaped, and include a first portion 154 and a second portion 156. The first portions 154 extend outwardly from the upper surface 142, and the second portions 156 extend from the first portions 154 inwardly toward the aperture 146. More specifically, a first end 160 of each of the first portions 154 is attached to the upper surface 142, and a second end 162 of each of the first portions 154 is attached to one of the second portions 156. The first portions 154 each include an inner surface 164, and second portions 156 each include an inner surface 166. The inner surfaces 164 and 166 of each of the catches 152, together with the upper surface 142 form a cleft or crevice 164 for receiving a portion of the flange 134 of the hub 102 therein. Given that each of the catches 152 are deflectable and the intermediate surface 137 is angled, the flange 134 can be pushed passed the second portions 156 of the catches 152 and press fit into the various clefts 164. After the flange 134 is seated in the various clefts 164, the upper surface 136 of the flange 134 contacts the inner surfaces 164, and the lower surface of the flange 134 contacts the upper surface 142. The adaptor 100 is capable of rotation relative to the hub 102, but the adaptor 100 is prevented from movement along the axis central axis $A_3$, when the flange 134 is press fit into the adaptor 100.

During use of the adaptor 100, the hub 102, and the screw 12, a portion of the head portion 14 of the screw 12 can initially be inserted through the second opening 124 into the internal cavity 120 of the hub 102 to facilitate attachment therebetween. The screw 12 can then be inserted through the aperture 146 to facilitate contact of the hub 102 with the adaptor 100. Thereafter, the flange 134 can be press fit into the adaptor 100. Next, a surgical tool or instrument can be engaged to the tool-engaging portion 26. The screw 12 can then be driven into bone via rotation thereof using the surgical tool or instrument. Due to friction between the hub 102 and the head portion 14 of the screw 12, and the friction between the adaptor 100 and the flange 134 of the hub 102, the hub 102 and the adaptor 100 can rotate with rotation of the screw 12 until the spikes 150 of the adaptor 100 ultimately contact and catch on the bone. When contacted and caught on the bone, the spikes 150 hold the adaptor 100 in position relative to the bone and prevent further rotation thereof. Given that the screw 12 can rotate relative to the hub 102, and the hub 102 can rotate relative to the adaptor 100, the screw 12 can continue to be driven into the bone until the adaptor 100, the hub 102, and the screw 12 are seated against the bone.

Figure 8:
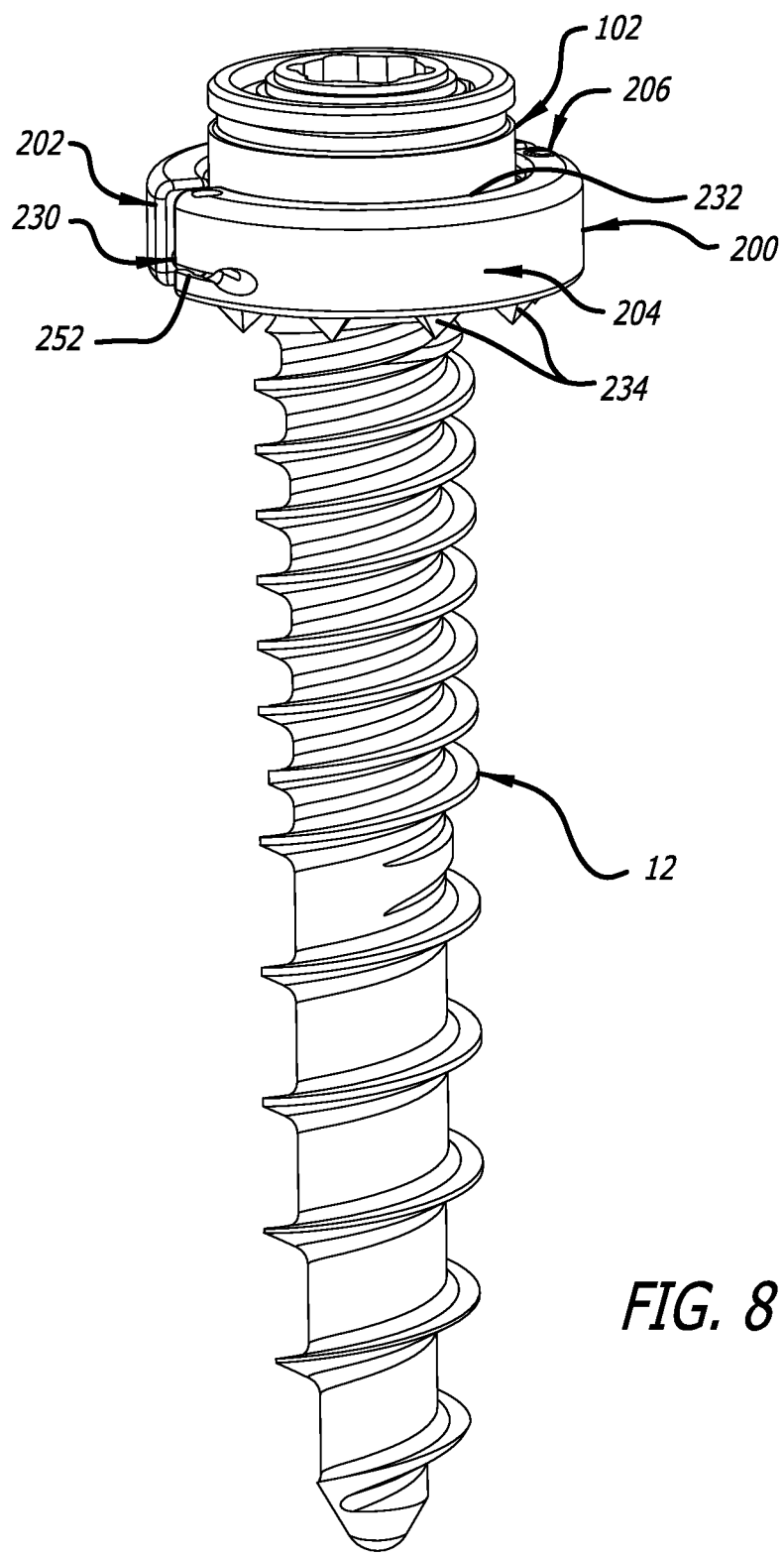
FIG. 8 is a top, front, perspective view that illustrates a third embodiment of an anatomy buttressing adaptor assembled with the hub of FIG. 4 and a screw.
Figure 9:
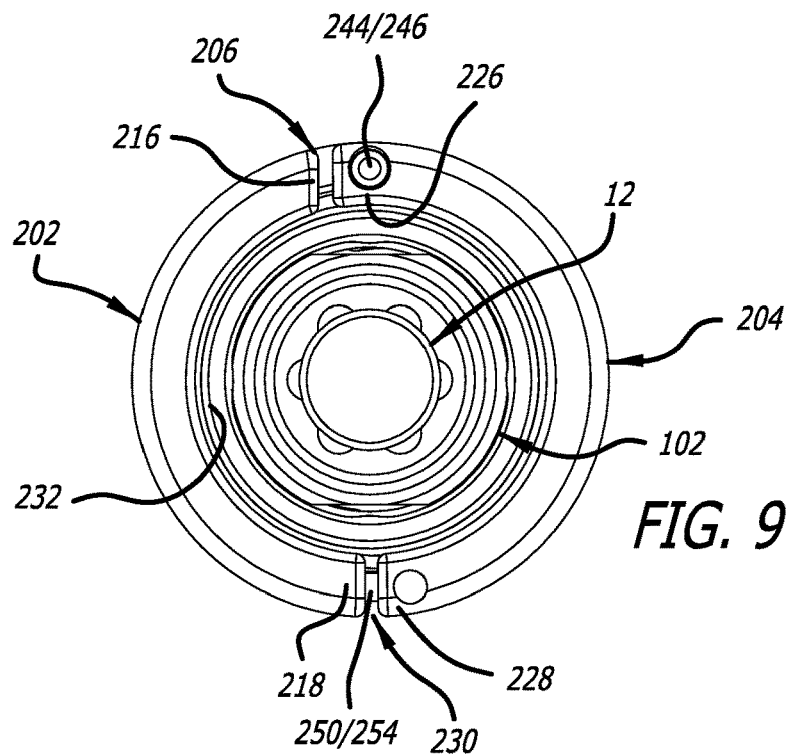
FIG. 9 is a top, plan view that illustrates the adaptor of FIG. 8 in an open first position.
Figure 10:
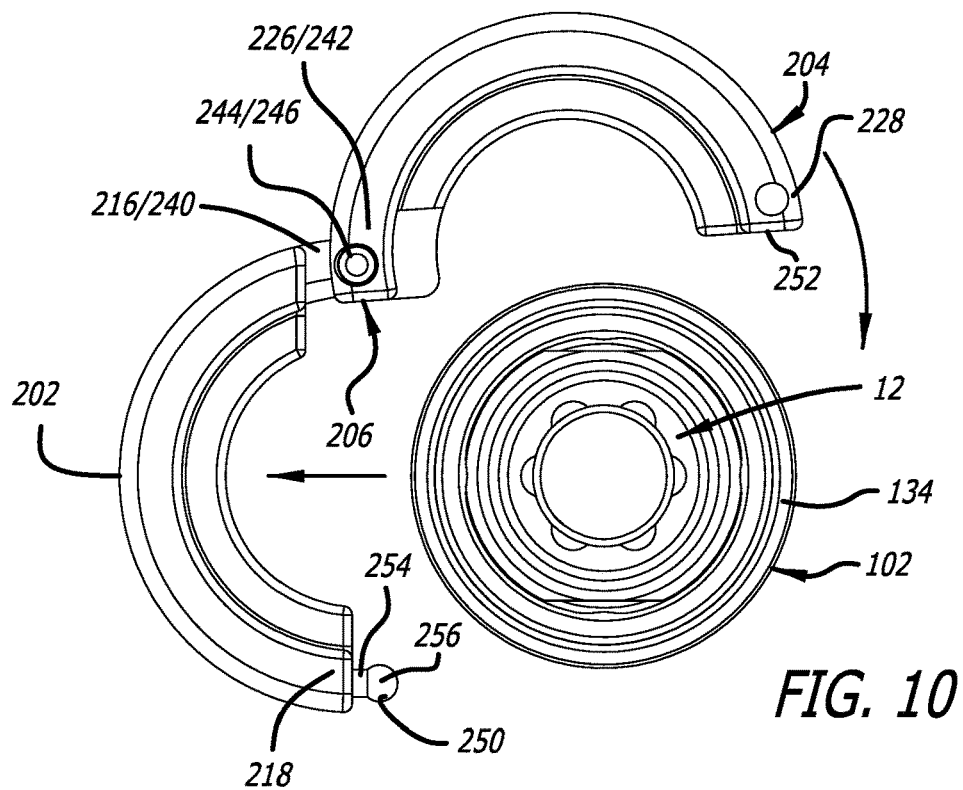
FIG. 10 is a top, plan view that illustrates the adaptor of FIG. 8 in a closed second position.

Another anatomy buttressing adaptor according to another embodiment of the present disclosure is generally indicated by the numeral 200 in FIGS. 8-10. The adaptor 200 can be used with the hub 102 and a fastener such as the screw 12. The adaptor 200 is attached to the hub 102, and the hub 102 and the screw 12 are attached to one another. Like with the adaptor 100 and the hub 102, the screw 12 can then be used to fixedly attach at least the adaptor 200, the hub 102, and the screw 12 to tissue such as, for example, bone.

As depicted in FIGS. 8-12, the adaptor 200 can be an annular structure including a first portion 202 and a second portion 204 hingedly attached to one another via a hinged connection 206. As depicted in FIGS. 9 and 10, each of the first portion 202 and the second portion 204 are approximately half of the annular structure of the adaptor 200. The first portion 202 includes an upper surface 210, a lower surface 212, a first channel 214, a first end 216, and a second end 218, and the second portion 204 includes an upper surface 220, a lower surface 222, a second channel 224, a first end 226, and a second end 228.

Figure 12:
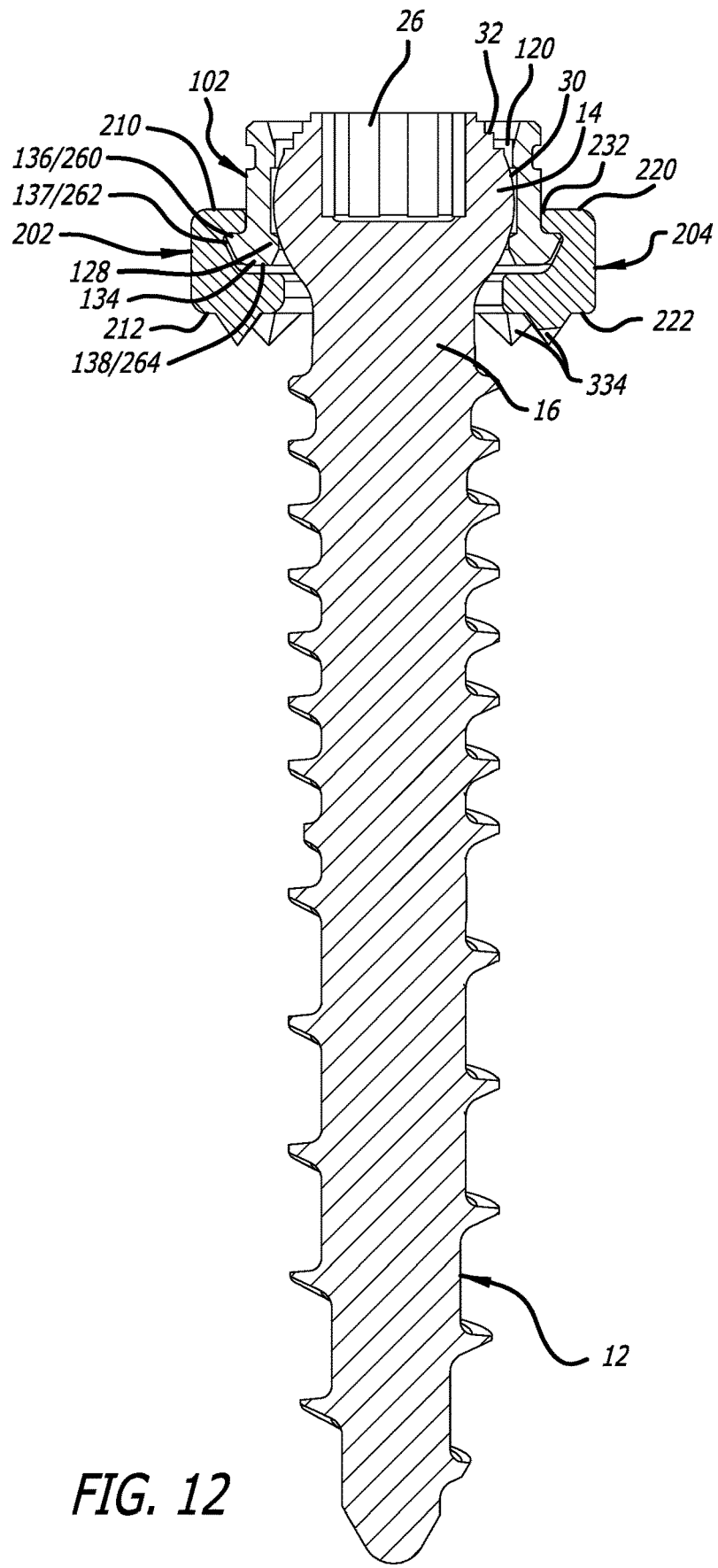
FIG. 12 is an elevational, side, cross-sectional view that illustrates the assembled adaptor, the hub, and the screw of FIG. 8.

The first end 216 of the first portion 202 and the first end 226 of the second portion 204 are attached to one another by the hinged connection 206, and the second end 218 of the first portion 202 and the second end 228 of the second portion 204 are attachable to one another via a connection mechanism 230. When the second ends 218 and 228 are attached to one another via the connection mechanism 230, an aperture 232 is formed that extends between the upper surfaces 210 and 220 and the lower surfaces 212 and 222. As discussed below, a portion of the body portion 110 of the hub 102 is ultimately received within the aperture 232, and portions of the flange 134 of the hub 102 is ultimately received within the first channel 214 and the second channel 224. Furthermore, the upper surfaces 210 and 220 and the lower surfaces 212 and 222 can be annular, and the lower surfaces 212 and 222 can include various protrusions 234 for engaging bone spaced therearound. As depicted in FIGS. 8 and 12, the protrusions 234 are spikes formed on (e.g., unitarily formed on) the lower surfaces 212 and 222 and configured to engage bone. As depicted in FIG. 8, for example, the spikes 234 can be formed as pyramids.

Figure 11:
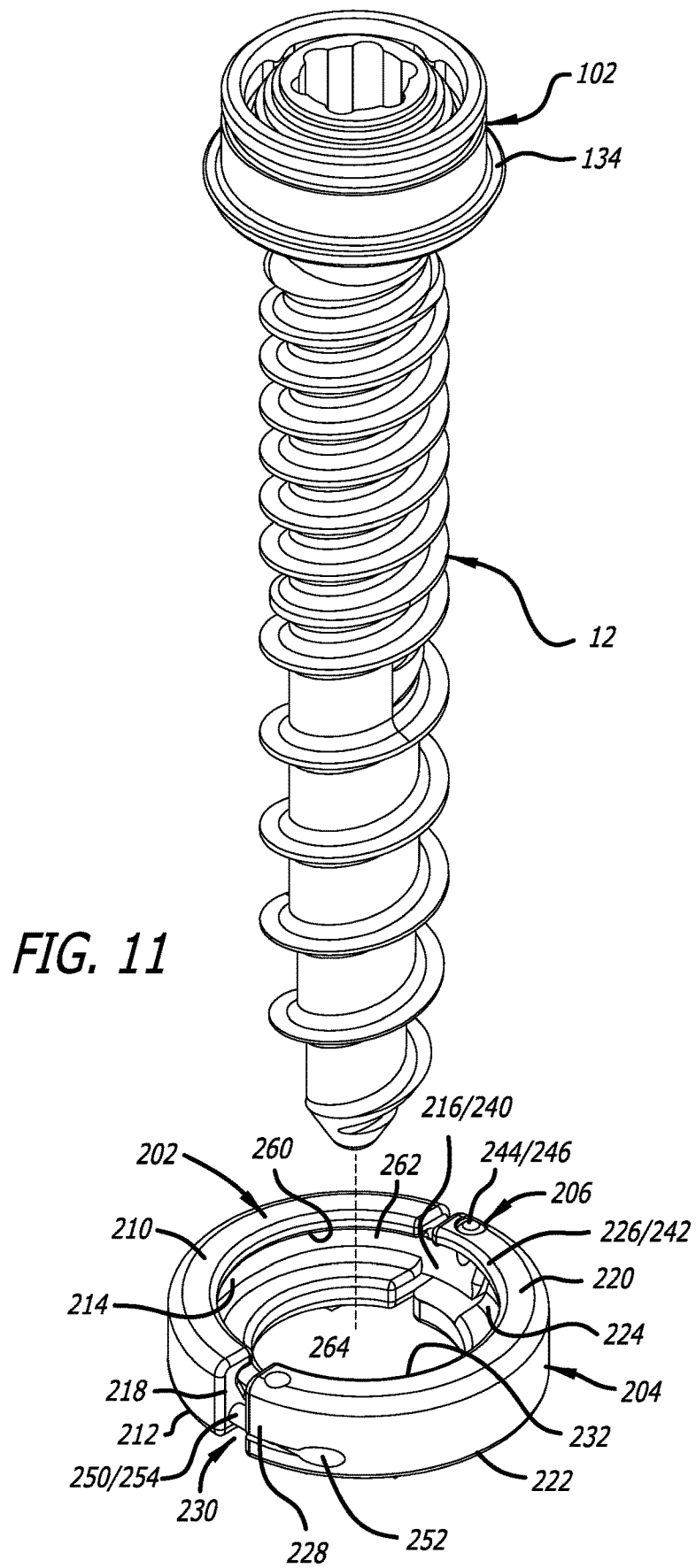
FIG. 11 is a partially exploded, top, front perspective view that illustrates the adaptor, the hub, and the screw of FIG. 8.

The hinged connection 206 can be formed as a clevis/tang arrangement, where one of the first ends 216 and 226 includes is a tang, and the other of the first ends 216 and 226 includes a clevis. As depicted in FIG. 11, the first end 216 includes a tang 240 and the second end 226 includes a clevis 242. The clevis 242 defines an area for receiving portions of the tang 240 therein, the tang 240 includes a first post 244 and a second post formed on opposite sides thereof, and the clevis 242 includes a first aperture 246 and a second aperture formed therein. To attach the first ends 216 and 226, the first post 244 is received in the first aperture 246, and the second post is received in the second aperture. The first post 244 and the second post can be configured to snap-fit into the first aperture 246 and the second aperture, respectively. After the first portion 202 and the second portion 204 have attached to one another using the hinged connection 206, the first portion 202 and the second portion 204 are pivotally moveable between at least a first position (FIG. 9) and a second position (FIG. 10).

The connection mechanism 230 can be formed as a snap fit connection, where one of the second ends 218 and 228 includes an aperture, and the other of the second ends 218 and 228 is a post received in the aperture. As depicted in FIGS. 9 and 11, the second end 218 includes a post 250, and the second end 228 includes an aperture 252 for receiving at least a portion of the post 250. The post 250 includes a shaft portion 254 and a head portion 256 attached to the shaft portion 254, and at least a portion of the head portion 256 is receivable in the aperture 252. At least a portion of the head portion 256 can be snap fit into the aperture 252 to facilitate attachment of the second ends 218 and 228 to one another.

As depicted in FIG. 12, each of the first channel 214 and the second channel 216 have cross-sections that are generally C-shaped with an upper surface 260, an intermediate surface 262, and a lower surface 264. After portions of the flange 134 are received in the first channel 214 and the second channel 224, the upper surface 136 of the flange 134 contacts the upper surfaces 260 of the first channel 214 and the second channel 224, the intermediate surface 137 of the flange 134 contacts the intermediate surfaces 262 of the first channel 214 and the second channel 224, and the lower surface 138 of the flange 134 contacts the lower surfaces 264 of the first channel 214 and the second channel 224. The adaptor 200 is capable of rotation relative to the hub 102, but the adaptor 200 is prevented from movement along the axis central axis $A_3$, when the flange 134 is press fit into the adaptor 100.

During use of the adaptor 200, the hub 102, and the screw 12, a portion of the head portion 14 of the screw 12 can initially be inserted through the second opening 124 into the internal cavity 120 of the hub 102 to facilitate attachment therebetween. Thereafter, the adaptor 200 can be closed around the hub 102 by moving the first portion 202 and the second portion 204 from the first position (FIG. 9) to the second position (FIG. 10), and receiving the flange 134 in the first channel 214 and the second channel 224. Next, a surgical tool or instrument can be engaged to the tool-engaging portion 26. The screw 12 can then be driven into bone via rotation thereof using the surgical tool or instrument. Due to friction between the hub 102 and the head portion 14 of the screw 12, and the friction between the adaptor 200 and the flange 134 of the hub 102, the hub 102 and the adaptor 200 can rotate with rotation of the screw 12 until the spikes 234 of the adaptor 200 ultimately contact and catch on the bone. When contacted and caught on the bone, the spikes 234 hold the adaptor 200 in position relative to the bone and prevent further rotation thereof. Given that the screw 12 can rotate relative to the hub 102, and the hub 102 can rotate relative to the adaptor 200, the screw 12 can continue to be driven into the bone until the adaptor 200, the hub 102, and the screw 12 are seated against the bone.

Figure 13:
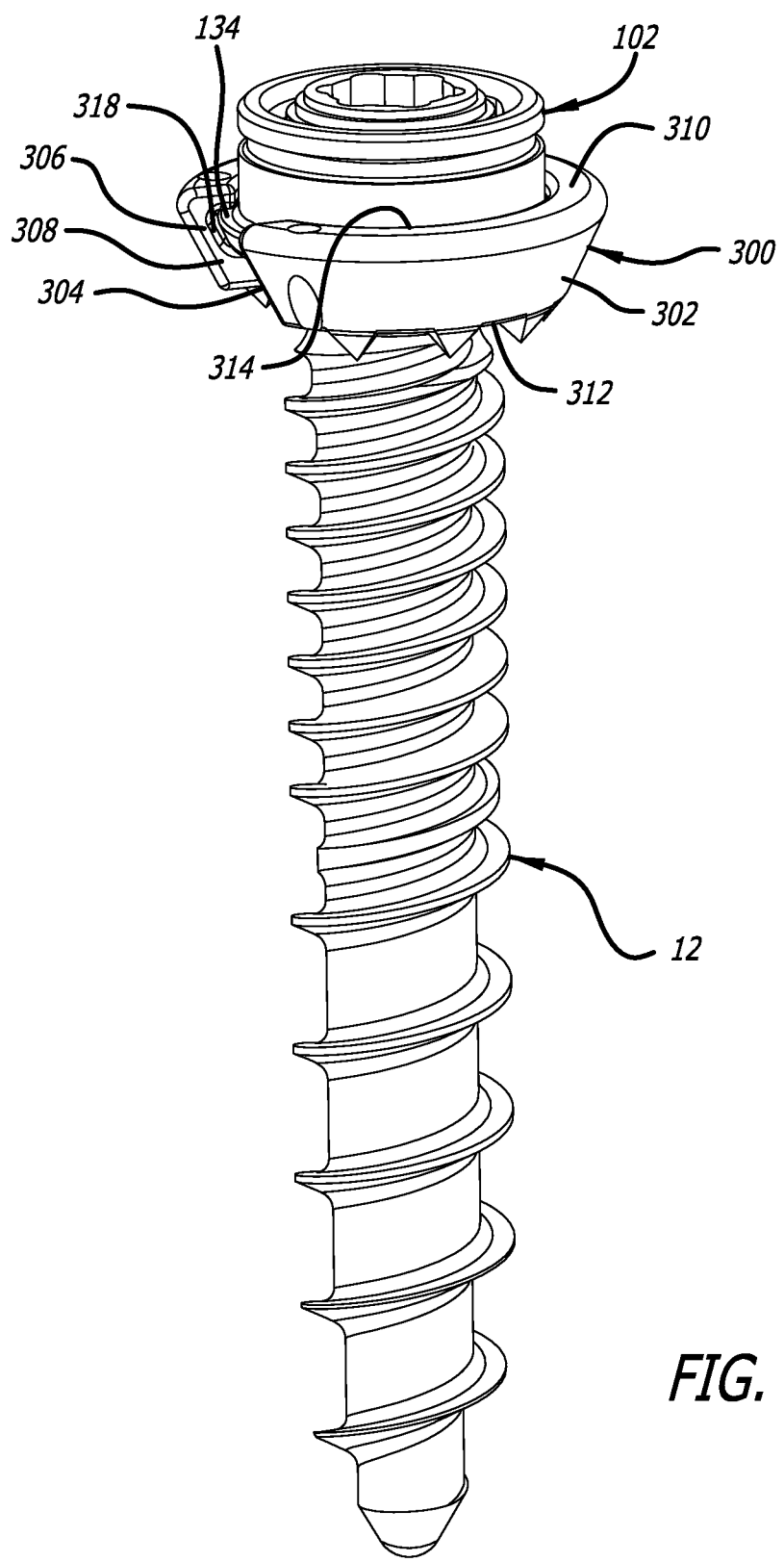
FIG. 13 is a top, front perspective view that illustrates a fourth embodiment of an anatomy buttressing adaptor assembled with the hub of FIG. 4 and a screw.
Figure 14:
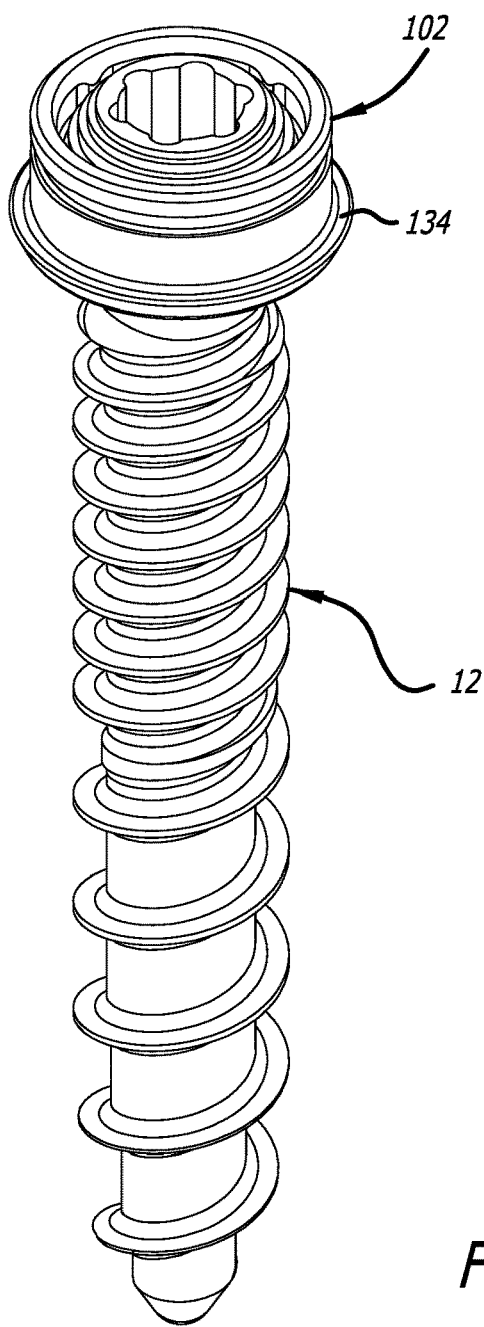
FIG. 14 is a partially exploded, top, front perspective view that illustrates the adaptor, the hub, and the screw of FIG. 13.
Figure 14:
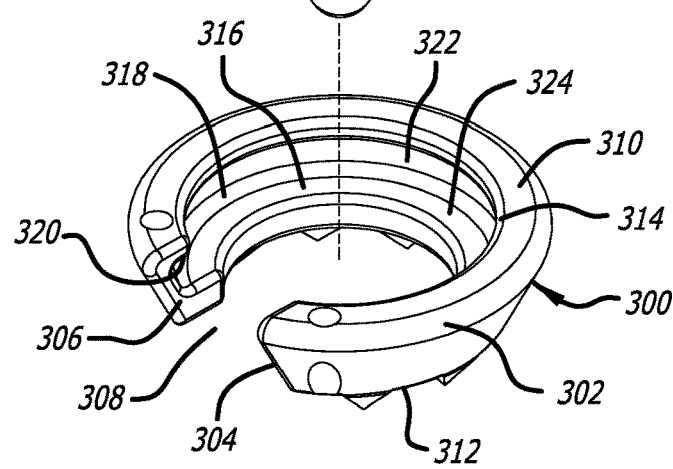
Figure 15:
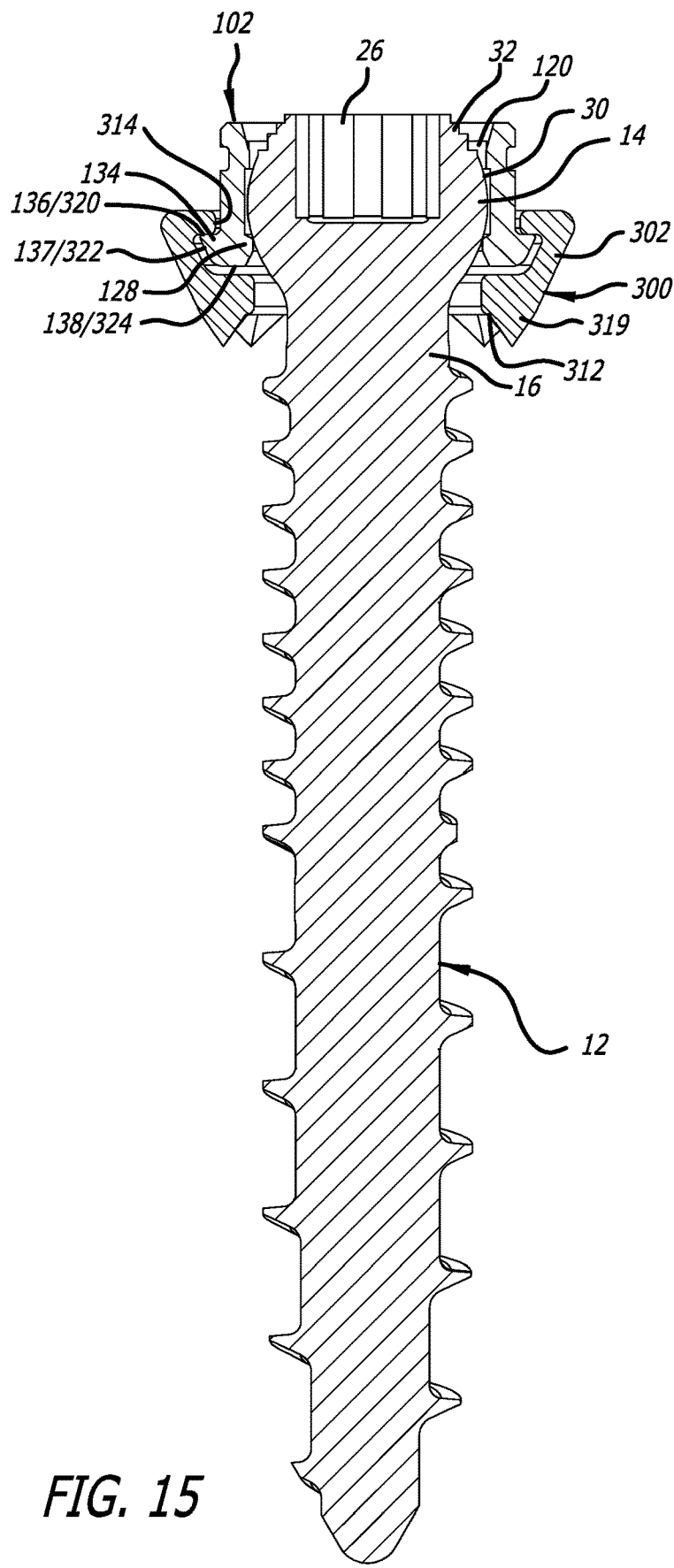
FIG. 15 is an elevational, side, cross-sectional view that illustrates the assembled adaptor, the hub, and the screw of FIG. 13.

Another anatomy buttressing adaptor according to another embodiment of the present disclosure is generally indicated by the numeral 300 in FIGS. 13-15. The adaptor 300 can be used with the hub 102 and a fastener such as the screw 12. The adaptor 300 is attached to the hub 102, and the hub 102 and the screw 12 are attached to one another. Like with the adaptor 200 and the hub 102, the screw 12 can then be used to fixedly attach at least the adaptor 300, the hub 102, and the screw 12 to tissue such as, for example, bone.

As depicted in FIGS. 13-15, the adaptor 300 including a body portion 302 that can be formed as an incomplete generally annular structure. The body portion 302 includes a first end 304 and a second end 306 spaced apart by a gap 308, an upper surface 310, a lower surface 312, an aperture 314 extending between the upper surface 310 and the lower surface 312, an internal cavity 316 defined at least in part by the aperture 314, and a channel 318 communicating with the internal cavity 316. The body portion 302 of the adaptor 300 is resiliently flexible to afford further spreading of the first end 304 and the second end 306 apart from one another, a portion of the body portion 110 of the hub 102 is ultimately received within the aperture 314, and a portion of the flange 134 of the hub 102 is ultimately received within the channel 318. Furthermore, the lower surface 312 can include various protrusions 319 spaced therearound. As depicted in FIGS. 13-15, the protrusions 319 are spikes formed on (e.g., unitarily formed on) the lower surface 312 and configured to engage bone. As depicted in FIG. 13, for example, the spikes 319 can be formed as pyramids.

As depicted in FIG. 15, the channel 318 has a cross-section that is generally C-shaped with an upper surface 320, an intermediate surface 322, and a lower surface 324. Given that the body portion 302 is resiliently flexible and the intermediate surface 137 is angled, the flange 134 (as the hub 102 is being inserted into adaptor 300) can be pushed passed the upper portion of the adaptor 300 and press fit into the channel 318. After portions of the flange 134 are received in the channel 318, the upper surface 136 of the flange 134 contacts the upper surface 320 of the channel 318, the intermediate surface 137 of the flange 134 contacts the intermediate surface 322 of the channel 318, and the lower surface 138 of the flange 134 contacts the lower surface 324 of the channel 318. The adaptor 300 is capable of rotation relative to the hub 102, but the adaptor 300 is prevented from movement along the axis central axis $A_3$, when the flange 134 is press fit into the adaptor 300.

During use of the adaptor 300, the hub 102, and the screw 12, a portion of the head portion 14 of the screw 12 can initially be inserted through the second opening 124 into the internal cavity 120 of the hub 102 to facilitate attachment therebetween. The screw 12 can then be inserted through the aperture 314 to facilitate contact of the hub 102 with the adaptor 300. Thereafter, the flange 134 can be press fit into the adaptor 300. Next, a surgical tool or instrument can be engaged to the tool-engaging portion 26. The screw 12 can then be driven into bone via rotation thereof using the surgical tool or instrument. Due to friction between the hub 102 and the head portion 14 of the screw 12, and the friction between the adaptor 300 and the flange 134 of the hub 102, the hub 102 and the adaptor 300 can rotate with rotation of the screw 12 until the spikes 319 of the adaptor 300 ultimately contact and catch on the bone. When contacted and caught on the bone, the spikes 319 hold the adaptor 300 in position relative to the bone and prevent further rotation thereof. Given that the screw 12 can rotate relative to the hub 102, and the hub 102 can rotate relative to the adaptor 300, the screw 12 can continue to be driven into the bone until the adaptor 300, the hub 102, and the screw 12 are seated against the bone.

Figure 16:
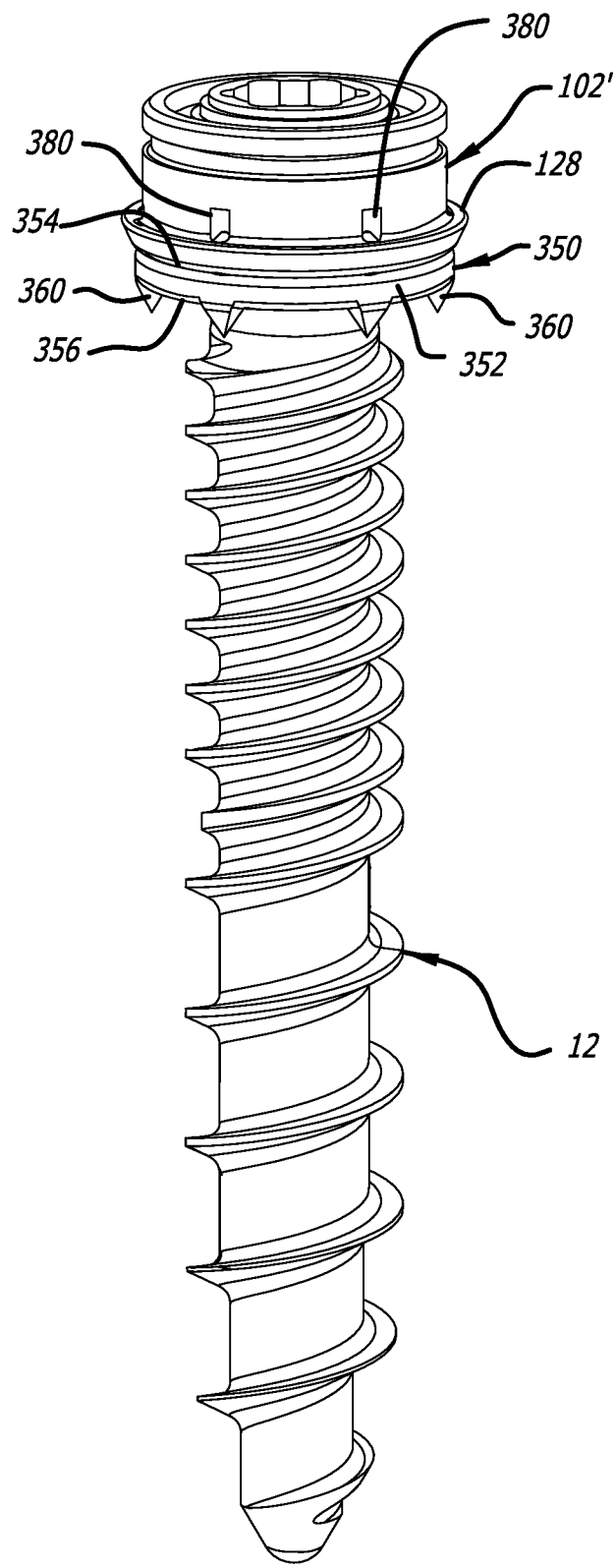
FIG. 16 is a top, front perspective view that illustrates a fifth embodiment of an anatomy buttressing adaptor assembly with the hub of FIG. 4 and a screw.
Figure 17:
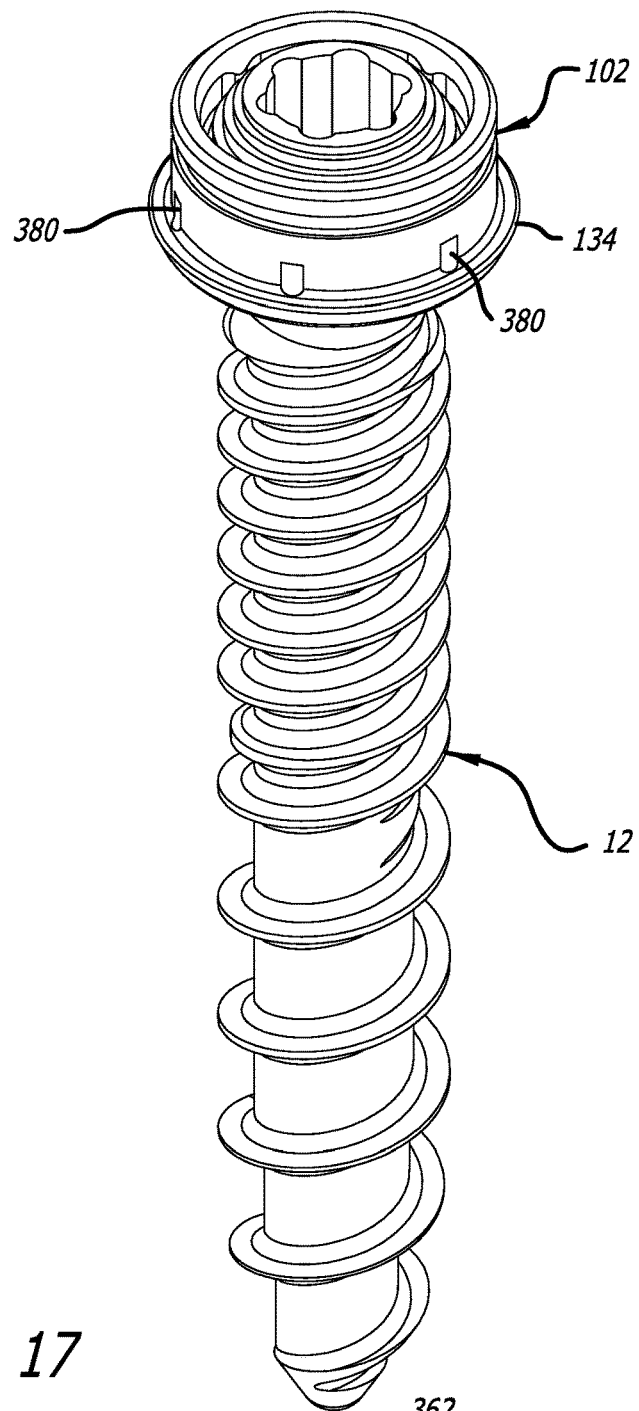
FIG. 17 is a partially exploded, top, front perspective view that illustrates the adaptor, the hub, and the screw of FIG. 16.
Figure 17:
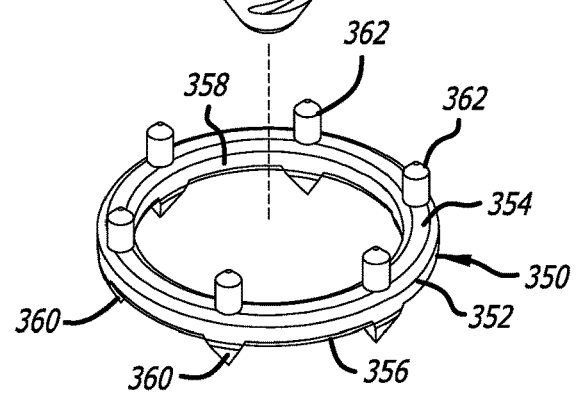
Figure 18:
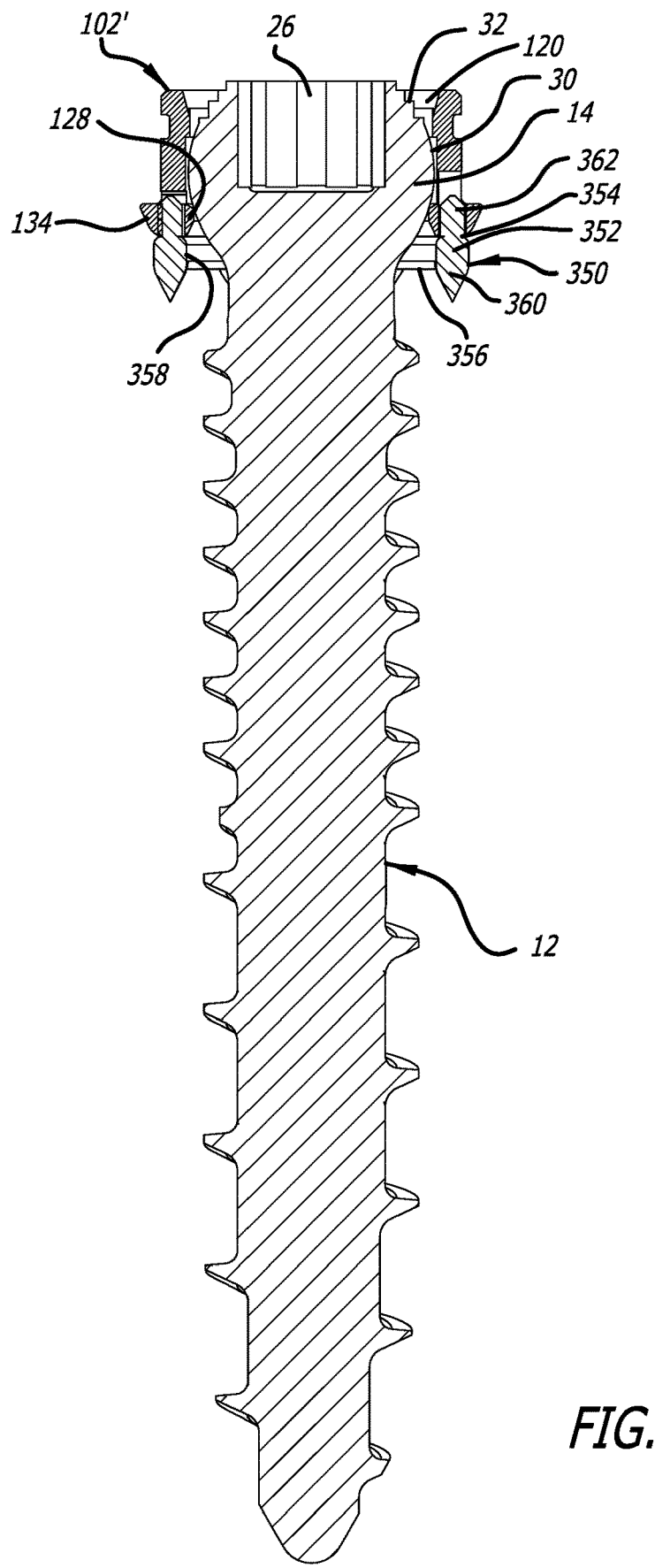
FIG. 18 is an elevational, side, cross-sectional view that illustrates the assembled adaptor, the hub, and the screw of FIG. 16.

Another anatomy buttressing adaptor according to another embodiment of the present disclosure is generally indicated by the numeral 350 in FIGS. 16-18. The adaptor 350 can be used with a hub 102' and a fastener such as the screw 12. The hub 102' is identical to the hub 102, but includes apertures/slots 380 extending through portions of the body portion 110 and the flange 134. The adaptor 350 is attached to the hub 102', and the hub 102' and the screw 12 are attached to one another. Like with the adaptor 300 and the hub 102', the screw 12 can then be used to fixedly attach at least the adaptor 350, the hub 102', and the screw 12 to tissue such as, for example, bone.

As depicted in FIGS. 16-18, the adaptor 350 including a base portion 352 that can be formed as an annular structure having an upper surface 354, a lower surface 356, an aperture 358 extending between the upper surface 354 and the lower surface 356. The upper surface 354 and the lower surface 356 can be annular, the lower surface 356 can include various protrusions 360 for engaging bone spaced therearound, and the upper surface 354 can include various posts spaced therearound. As depicted in FIGS. 16-18, the protrusions 360 are spikes formed on (e.g., unitarily formed on) the lower surface 356 and configured to engage bone, and posts 362 are formed on (e.g., unitarily formed on) with the upper surface 354 and configured to be received in the apertures/slots 380. As depicted in FIG. 16, for example, the spikes 360 can be formed as pyramids.

During use of the adaptor 350, the hub 102', and the screw 12, a portion of the head portion 14 of the screw 12 can initially be inserted through the second opening 124 into the internal cavity 120 of the hub 102' to facilitate attachment therebetween. The screw 12 can then be inserted through the aperture 358 to facilitate contact of the hub 102' with the adaptor 350. Thereafter, the adaptor 350 can be engaged to the hub 102' by inserting each of the posts 362 into a corresponding one of the aperture/slots 380. Next, a surgical tool or instrument can be engaged to the tool-engaging portion 26. The screw 12 can then be driven into bone via rotation thereof using the surgical tool or instrument. Due to friction between the hub 102' and the head portion 14 of the screw 12, and the engagement between the adaptor 350 and the hub 102', the hub 102' can rotate and the adaptor 350 rotates with rotation of the screw 12. When contacted and caught on the bone, the spikes 360 hold the adaptor 350 in position relative to the bone. Given that the screw 12 can rotate relative to the hub 102', and the hub 102' can rotate relative to the adaptor 350, the screw 12 can continue to be driven into the bone until the adaptor 350, the hub 102, and the screw 12 are seated against the bone.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

We claim:

1. A system comprising:
a screw having a head portion, a shaft portion, and a central axis; and
an anatomy buttressing adaptor including a body portion having a first end, an opposite second end, a height measured between the first end and the second end, an upper surface at the first end, a lower surface at the second end, a substantially cylindrical exterior surface, a substantially cylindrical interior surface, an internal cavity extending through the body portion, a first opening through the upper surface and communicating with the internal cavity, a second opening through the lower surface and communicating with the internal cavity, an annular flange extending into the internal cavity adjacent the second end, and spikes formed on and spaced around the lower surface, the internal cavity formed at least in part by the substantially cylindrical interior surface and the annular flange, the substantially cylindrical interior surface extending between the first opening and the annular flange, the internal cavity having a central axis extending through the first end and the second end of the body portion, the annular flange being positioned at least adjacent the second end of the body portion, and each of the spikes abutting the cylindrical exterior surface, each of the spikes including a generally triangular cross section and having an exterior surface continuous with the cylindrical exterior surface,
wherein at least a portion of the screw is insertable through the first opening, the internal cavity, and the second opening, at least a portion of the head portion is confinable within the internal cavity, and the screw, during confinement of at least a portion of the head portion within the internal cavity, is rotatable about the central axis thereof and is pivotal relative to the central axis of the body portion; and
wherein the body portion further comprises at least two protrusions formed on the substantially cylindrical interior surface intermediate the first end and the annular flange, the at least two protrusions extending into the internal cavity, and the portion of the head portion is confinable within the internal cavity between the at least two protrusions and the annular flange, and wherein portions of the head portion of the screw can be inserted past the at least two protrusions and snap-fit into the internal cavity.

2. The system of claim 1, wherein the annular flange defines at least a portion of the second opening in the body portion, and the annular flange prevents at least a portion of the head portion of the screw from exiting the internal cavity via the second opening in the body portion.

3. The system of claim 1, wherein the screw further comprises a neck portion between the head portion and the shaft portion, the head portion is generally spherical, and portions of the generally-spherical head portion contact the annular flange and afford pivotal movement of the screw relative to the central axis of the body portion.

4. The system of claim 1, wherein, during pivotal movement of the screw relative to the central axis of the body portion, the central axis of the screw can be angularly adjusted relative to the central axis of the internal cavity.

5. The system of claim 1, wherein the shaft portion can be inserted through the first opening, the internal cavity, and the second opening, and, to facilitate attachment of the screw and the anatomy buttressing adaptor, the head portion can be inserted through the first opening and into to the internal cavity to confine the portion of the head portion in the internal cavity.

6. The system of claim 5, wherein the screw and the buttressing adaptor are engageable to bone, and, to facilitate such engagement, the screw can first be engaged to bone, the anatomy buttressing adaptor can second be engaged to bone, and the screw can third rotate relative to the anatomy buttressing adaptor until the screw is seated against the anatomy buttressing adaptor.

7. The system of claim 1, wherein each of the spikes include a pointed tip, and each of the spikes are configured to engage bone.

8. The system of claim 1, wherein first plane perpendicular to the central axis of the internal cavity bisects the height of the body portion, and each of the at least two protrusions are positioned adjacent an intersection of the first plane with the substantially cylindrical interior surface.

9. The system of claim 8, wherein each of the at least two protrusions are closer to the central axis of the internal cavity than the annular flange portion.

10. A system comprising:
a screw having a head portion, a shaft portion, and a central axis; and
an anatomy buttressing adaptor including a body portion having a first end, an opposite second end, a height measured between the first end and the second end, a central axis extending through the first end and the second end, an annular lower surface at the second end, a substantially cylindrical exterior surface, a substantially cylindrical interior surface, an internal cavity extending through the body portion, a first opening through the first end and communicating with the internal cavity, a second opening through the second end and communicating with the internal cavity, an annular flange extending into the internal cavity adjacent the second end, and spikes spaced around the annular lower surface, the cylindrical exterior surface having a maximum radius centered on the central axis of the body portion, the internal cavity formed at least in part by the substantially cylindrical interior surface and the annular flange, the substantially cylindrical interior surface extending between the first opening and the annular flange, the annular flange being positioned at least adjacent the second end of the body portion, each of the spikes abutting the cylindrical exterior surface, each of the spikes including a generally triangular exterior surface continuous with the cylindrical exterior surface, and at least a portion of the spikes being located at and adjacent the maximum radius of the cylindrical exterior surface, wherein the screw, during confinement of at least a portion of the head portion within the internal cavity, is rotatable about the central axis thereof and is pivotal relative to the central axis of the body portion; and wherein the body portion further comprises at least two protrusions formed on the substantially cylindrical interior surface and extending into the internal cavity, and wherein a first plane perpendicular to the central axis of the internal cavity bisects the height of the body portion, and each of the at least two protrusions are positioned adjacent an intersection of the first plane with the substantially cylindrical interior surface.

11. The system of claim 10, wherein each of the spikes include a pointed tip, and each of the spikes are configured to engage bone.

12. The system of claim 10, wherein each of the at least two protrusions are closer to the central axis of the internal cavity than the annular flange portion.

13. A system comprising:
a screw having a head portion, a shaft portion, and a central axis; and
an anatomy buttressing adaptor including a body portion having a first end, an opposite second end, a height measured between the first end and the second end, a central axis extending through the first end and the second end, an annular lower surface at the second end, a substantially cylindrical exterior surface, a substantially cylindrical interior surface, a thickness measured between the substantially cylindrical exterior surface and the substantially cylindrical interior surface in a flat first plane perpendicular to the central axis of the body portion, an internal cavity extending through the body portion, a first opening through the upper surface and communicating with the internal cavity, a second opening through the annular lower surface and communicating with the internal cavity, an annular flange extending into the internal cavity adjacent the second end, and spikes spaced around the annular lower surface, the internal cavity formed at least in part by the substantially cylindrical interior surface and the annular flange, the substantially cylindrical interior surface extending between the first opening and the annular flange, the internal cavity having a central axis extending through the first end and the second end of the body portion, the annular flange being positioned at least adjacent the second end of the body portion, each of the spikes abutting the cylindrical exterior surface, each of the spikes including a generally triangular exterior surface continuous with the cylindrical exterior surface, and at least one of the spikes having a maximum dimension in planes perpendicular the central axis of the body portion substantially equal to the thickness measured between the substantially cylindrical exterior surface and the substantially cylindrical interior surface, wherein the screw, during confinement of at least a portion of the head portion within the internal cavity, is rotatable about the central axis thereof and is pivotal relative to the central axis of the body portion; and wherein the body portion further comprises at least two protrusions formed on the substantially cylindrical interior surface and extending into the internal cavity, and wherein a second plane perpendicular to the central axis of the internal cavity bisects the height of the body portion, and each of the at least two protrusions are positioned adjacent an intersection of the second plane with the substantially cylindrical interior surface.

14. The system of claim 13, wherein each of the spikes include a pointed tip, and each of the spikes are configured to engage bone.

* * * * *